(12) United States Patent
Kaula et al.

(10) Patent No.: US 8,798,768 B2
(45) Date of Patent: Aug. 5, 2014

(54) ELECTRICALLY IDENTIFIABLE ELECTRODE LEAD AND METHOD OF ELECTRICALLY IDENTIFYING AN ELECTRODE LEAD

(75) Inventors: Norbert Kaula, Arvada, CO (US); Jeff A. Weisgarber, Jewett, OH (US); Yohannes Iyassu, Denver, CO (US)

(73) Assignee: Greatbatch Ltd., Clarence, NY (US)

( * ) Notice: Subject to any disclaimer, the term of this patent is extended or adjusted under 35 U.S.C. 154(b) by 87 days.

(21) Appl. No.: 13/174,113

(22) Filed: Jun. 30, 2011

(65) Prior Publication Data

US 2013/0006333 A1 Jan. 3, 2013

(51) Int. Cl.
*A61N 1/372* (2006.01)

(52) U.S. Cl.
USPC ........................................... 607/116

(58) Field of Classification Search
USPC .................................. 607/116, 118
See application file for complete search history.

(56) References Cited

U.S. PATENT DOCUMENTS

| 6,385,593 | B2 | 5/2002 | Linberg |
| 6,675,049 | B2 * | 1/2004 | Thompson et al. ............. 607/60 |
| 6,687,544 | B1 | 2/2004 | Levine et al. |
| 7,016,726 | B1 | 3/2006 | Picardo et al. |
| 7,139,613 | B2 | 11/2006 | Reinke et al. |
| 7,239,916 | B2 | 7/2007 | Thompson et al. |
| 7,743,151 | B2 | 6/2010 | Vallapureddy et al. |

| 2003/0018369 | A1 | 1/2003 | Thompson |
| 2005/0246006 | A1 * | 11/2005 | Daniels ......................... 607/117 |
| 2011/0004076 | A1 | 1/2011 | Janna et al. |
| 2011/0112609 | A1 * | 5/2011 | Peterson ........................ 607/59 |

FOREIGN PATENT DOCUMENTS

| EP | 2540339 | 1/2013 |
| WO | 2005/105201 | 11/2005 |
| WO | 2011/057213 | 5/2011 |

OTHER PUBLICATIONS

European Extended Search Report for Application No. 12173229.1 dated Sep. 3, 2012 (6 pages).

* cited by examiner

*Primary Examiner* — Amanda Patton
(74) *Attorney, Agent, or Firm* — Michael Best & Friedrich LLP

(57) ABSTRACT

An electrically identifiable medical electrode lead. The lead includes a flexible lead body having a distal end and a connector end. The lead also includes a plurality of electrodes disposed near the distal end of the flexible lead body. The lead further includes a connector disposed at the connector end of the flexible lead body, the connector including a plurality of contacts. The lead additionally includes a plurality of conductors supported by and passing through the flexible lead body, the plurality of conductors including electrical conductors that provide paths for electrical current from the connector to the plurality of electrodes. Finally, the lead includes a memory circuit supported by the flexible lead body and being in electrical communication with a contact of the plurality of contacts in the connector.

21 Claims, 13 Drawing Sheets

ELECTRICALLY IDENTIFIABLE ELECTRODE LEAD AND METHOD OF ELECTRICALLY IDENTIFYING AN ELECTRODE LEAD

BACKGROUND

The invention relates to electrically identifiable electrode leads and methods of electrically identifying medical electrode leads, such as an implantable medical electrode lead. An exemplary implantable medical electrode lead can be used with an implantable pulse generator (IPG) of an electrical stimulation system.

When a physician implants multiple leads and connects them to an IPG, for example, the positions of the leads and the characteristics of the individual leads may be unknown, for example to the clinician programmer. Thus, confusion may arise of what locations and characteristics of the individual leads relate to what stimulation channel, after they have been implanted.

Currently, when information about implanted leads is recorded, it is typically done manually and before the implantation has occurred. For example, during surgery, a lead packaging will be opened and the brand, model, and serial number recorded by hand into the patient's medical record or into a clinician programmer device. Further, a manual assignment is required of the lead connected to the bore of the IPG header. These manual entries leave room for error in the process of recording information and may lead to false stimulation programming. Thus, what is needed are means and methods for accurately, quickly, and reliably determining what types of leads are connected to an IPG and their respective positions within the patient.

SUMMARY

In one aspect, the invention provides an electrically identifiable medical electrode lead. The lead includes a flexible lead body having a distal end and a connector end. The lead also includes a plurality of electrodes disposed near the distal end of the flexible lead body. The lead further includes a connector disposed at the connector end of the flexible lead body, the connector including a plurality of contacts. The lead additionally includes a plurality of conductors supported by and passing through the flexible lead body, the plurality of conductors including electrical conductors that provide paths for electrical current from the connector to the plurality of electrodes. Finally, the lead includes a memory circuit supported by the flexible lead body and being in electrical communication with a contact of the plurality of contacts in the connector.

In another aspect, the invention provides an electrical stimulation system. The electrical stimulation system includes an electrically identifiable medical electrode lead and an implantable pulse generator having a connection for at least one lead. The electrically identifiable medical electrode lead includes a flexible lead body having a distal end and a connector end; a plurality of electrodes disposed near the distal end of the flexible lead body; a connector disposed at the connector end of the flexible lead body, the connector including a plurality of contacts; a plurality of conductors supported by and passing through the flexible lead body, the plurality of conductors including electrical conductors that provide paths for electrical current from the connector to the plurality of electrodes; and a first memory circuit supported by the flexible lead body and being in electrical communication with a contact of the plurality of contacts in the connector.

In yet another aspect, the invention provides a method of electrically identifying an implantable medical electrode lead. The lead includes a flexible lead body having a distal end and a connector end. The lead also includes a plurality of electrodes disposed near the distal end of the flexible lead body. The lead further includes a connector disposed at the connector end of the flexible lead body, the connector including a plurality of contacts. The lead additionally includes a plurality of conductors supported by and passing through the flexible lead body, the plurality of conductors including electrical conductors that provide paths for electrical current from the connector to the plurality of electrodes. Finally, the lead includes a memory circuit supported by the flexible lead body and being in electrical communication with at least two contacts of the plurality of contacts in the connector. The method includes steps of coupling the lead to an electrical stimulation system; powering the at least two contacts that are in electrical communication with the memory circuit including electrically stimulating the at least two contacts to generate a voltage difference between the at least two contacts; and reading the identification code from the memory circuit in response to powering the at least two contacts.

In still another aspect, the invention provides an electrically identifiable medical lead extension. The electrically identifiable medical lead extension includes a flexible extension body having a proximal end and a distal end; a proximal connector disposed at the proximal end of the flexible extension body, the proximal connector including a plurality of contacts; a distal connector disposed at the distal end of the flexible extension body, the distal connector including a second plurality of contacts; a plurality of conductors supported by and passing through the flexible extension body, the plurality of conductors including electrical conductors that provide paths for electrical current from the proximal connector to the distal connector; and a memory circuit supported by the flexible extension body and being in electrical communication with a contact of the plurality of contacts.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The invention herein relates to a medical electrode lead for an electrical stimulation system. The electrical stimulation system provides stimulation to a target tissue of a patient, where the lead includes a non-radio frequency electrical mechanism by which the lead can be identified using wiring in the lead. In the construction shown, a spinal cord stimulation (SCS) system 100 provides electrical pulses to a patient, including to the neurons of the spinal cord of a patient, thereby providing treatment to the patient. However, other electrical stimulation systems can be used with the invention. The electrical stimulation system may provide electrical pulses to other portions of a patient's body, including a muscle or muscle group, peripheral nerves, the brain, etc.

In various implementations, the SCS system 100 includes a clinician programmer (CP) 130, a patient programmer and charger (PPC) 135, and a user programmer (UP) 140. The IPG 115 communicates with any one of the CP 130, the PPC 135, and the UP 140. The CP 130 interacts with the IPG 115 to develop a program (or protocol) for stimulating the patient, which may be facilitated through the use of a patient feedback device (PFD) 145. Once a protocol is developed, the PPC 135 or the UP 140 can activate the protocol. The protocol may be stored at the IPG 115 or can be communicated and stored at the PPC 135 or the UP 140. The PPC 135 also is used for charging the IPG 115. Constructions of the IPG 115, CP 130, PPC 135, and PP 140 are disclosed in U.S. patent application Ser. Nos. 13/118,764 and 13/118,775, both of which are incorporated herein by reference above.

Referring back to FIG. 1, a user may provide feedback to the CP 130 with the PFD 145 while the CP 130 develops the protocol for the IPG 115. In the construction shown in FIG. 1, the PFD 145 is an ergonomic handheld device having a sensor (also referred to as input) 165, a controller, and a communications output 175. Further description of the PFD 145 and methods for developing a protocol are disclosed in U.S. patent application Ser. Nos. 13/118,764 and 13/118,775, both of which have been incorporated by reference above.

Figure 1:
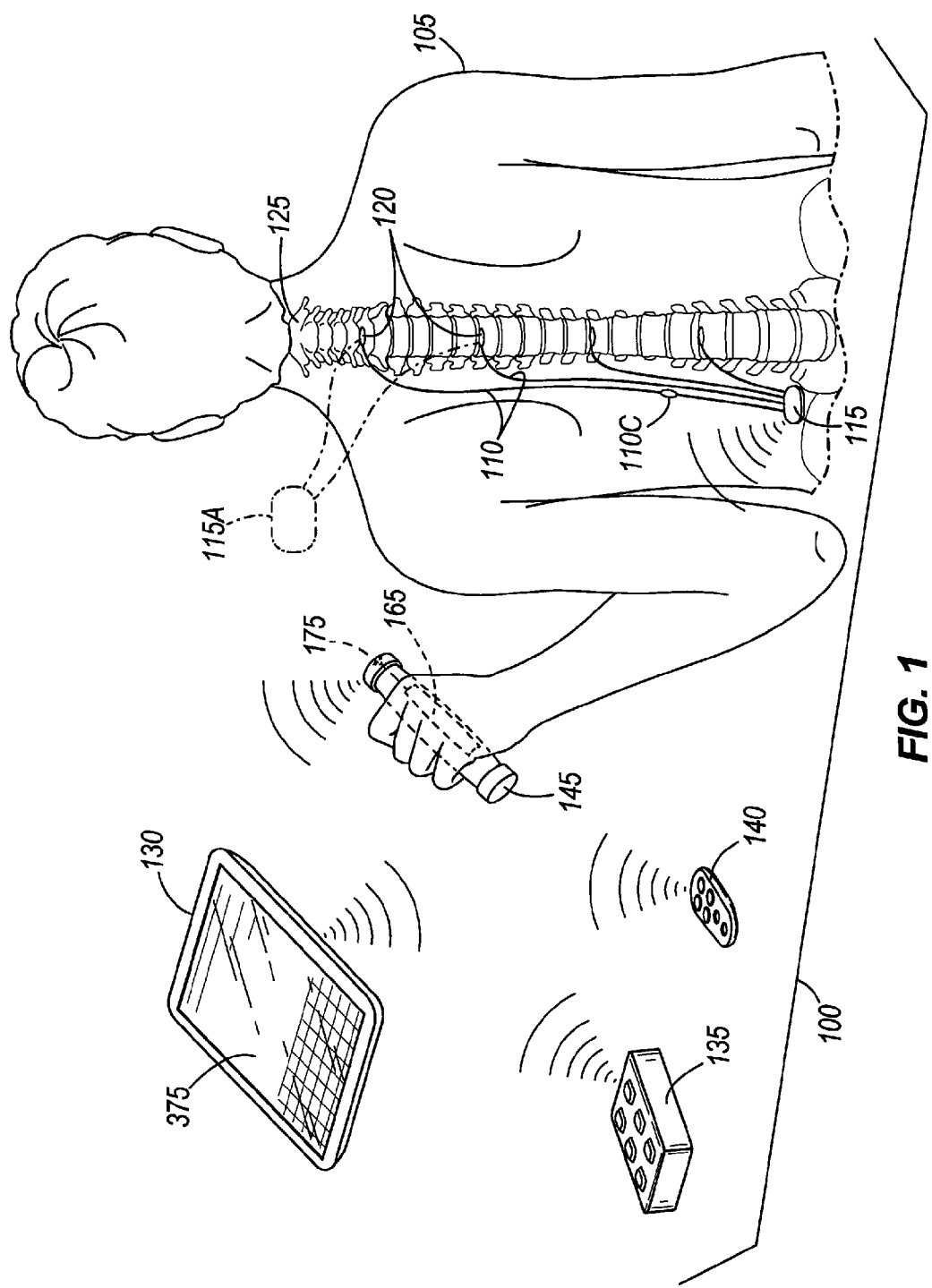
FIG. 1 is a partial perspective view of a patient receiving treatment with a spinal cord stimulation system.
Figure 2A:
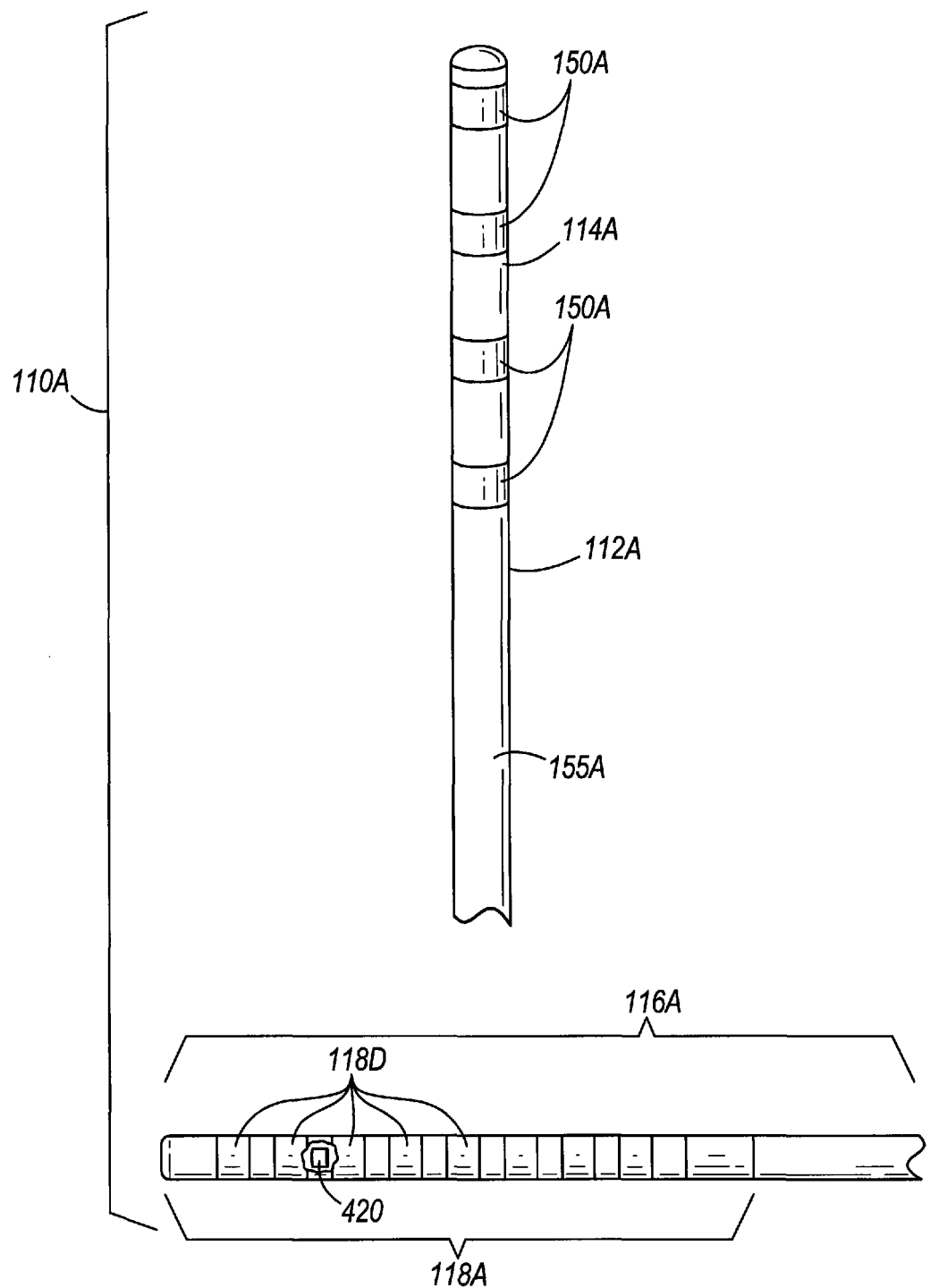
FIG. 2A is a perspective view of an in-line lead for use in the spinal cord stimulation system of FIG. 1.
Figure 2B:
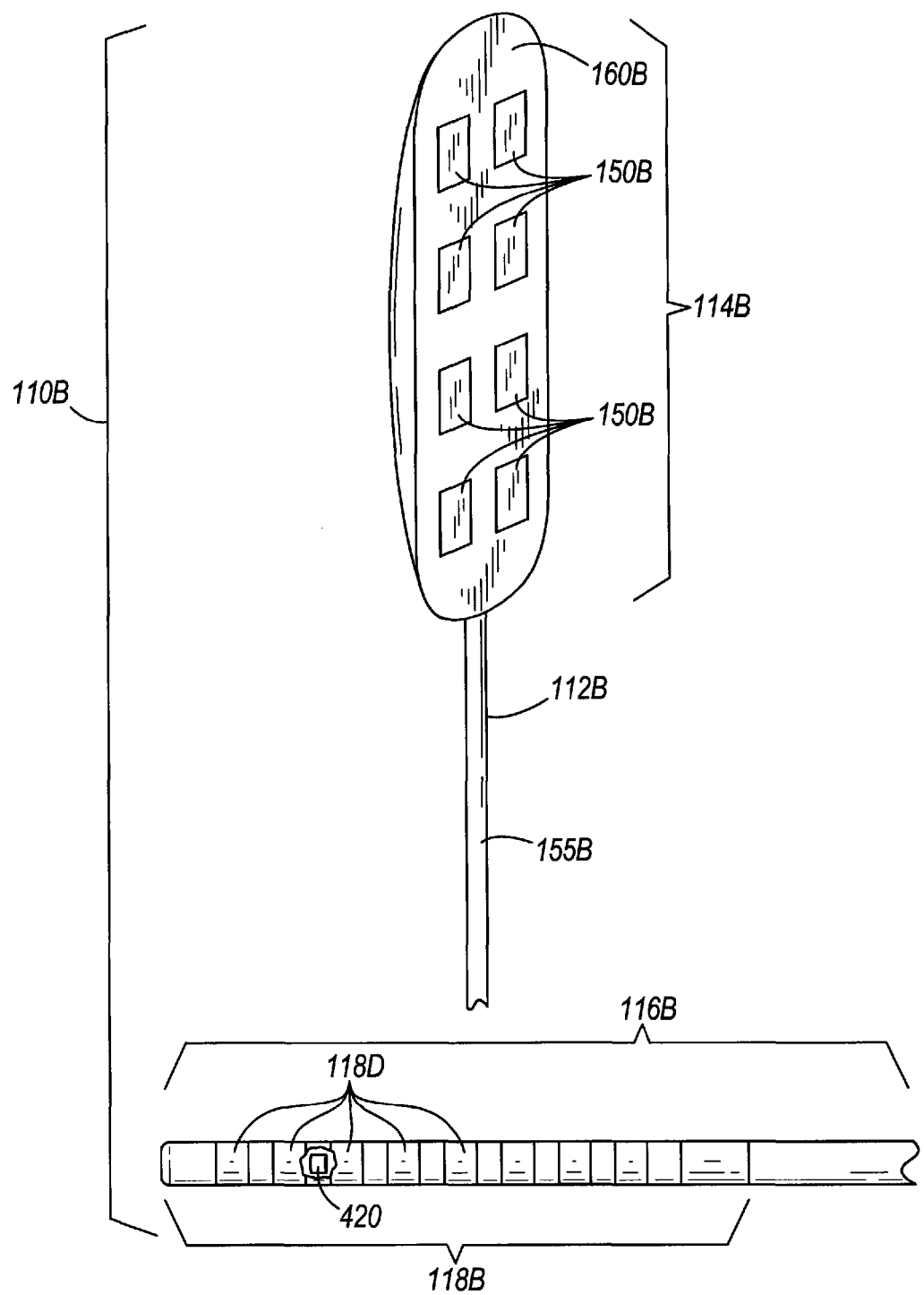
FIG. 2B is a perspective view of a paddle lead for use in the spinal cord stimulation system of FIG. 1.

Referring now to FIGS. 2A and 2B, the figures show two exemplary medical electrode leads 110A and 110B, respectively, that can be used in the SCS system 100. A first common type of lead is the "in-line" lead 110A shown in FIG. 2A. An in-line lead 110A includes individual electrodes 150A along the length of a flexible cable 155A. A second common type of lead is the "paddle" lead 110B shown in FIG. 2B. In general, the paddle lead 110B is shaped with a wide platform 160B on which a variety of electrode 150B configurations are situated. For example, the paddle lead 110B shown in FIG. 2B has two columns of four rectangular shaped electrodes 150B. A paddle lead typically contains electrodes on one side only, however, in various embodiments a paddle lead 110B can include electrodes 150B on both sides. Furthermore, although the embodiment shown in FIG. 2B shows the electrodes 150B embedded within the paddle lead 110B, in other embodiments a paddle lead 110B can include electrodes 150B that are mounted on the surface. A lead extension 110C, shown in FIGS. 1 and 3, optionally connects the lead 110A, 110B to the IPG 115.

For both leads shown in FIGS. 2A and 2B, a flexible cable 155A or 155B has respective small conductors (e.g. wires) for the electrodes 150A or 150B. The conductors are embedded within the cable 155A or 155B and carry the electrical stimulation from the IPG 115 to the electrodes 150A or 150B.

It is envisioned that other types of medical electrode leads 110 and electrode arrays 120 can be used with the invention. Also, the number of electrodes 150 and how the electrodes 150 are arranged in the electrode array 120 can vary from the examples discussed herein.

The leads shown in FIGS. 2A and 2B are multiple channel leads. Here, a "channel" is defined as a specified electrode 150, or group of electrodes 150, that receives a specified pattern or sequence of electrical stimuli. For simplicity, this description will focus on each electrode 150 and the IPG's 115 metallic housing providing a respective channel. When more than one channel is available, each channel may be programmed to provide its own stimulus to its defined electrode.

There are many instances when it is advantageous to have multiple channels for stimulation. For example, different pain locations (e.g., upper extremities, lower extremities) of the patient may require different stimuli. Further, some patients may exhibit conditions better suited to "transverse" stimulation paths, where the current paths travel across the spinal column, while other patients may exhibit conditions better suited to "longitudinal" stimulation paths, where the current paths travel along the spinal column. Therefore, multiple electrodes positioned to provide multiple channels can cover more tissue/neuron area, and thereby provide better stimulation protocol flexibility to treat the patient.

It is also envisioned that the number of leads 110 can vary. For example, one, two, or more leads 110 can be connected to the IPG 115. The electrode arrays 120 of the leads 110, respectively, can be disposed in different vertical locations on the spine 125 to achieve longitudinal stimulation, can be disposed horizontally (or "side-by-side") on the spine 125 to achieve transverse stimulation, or some combination thereof.

Figure 4A:
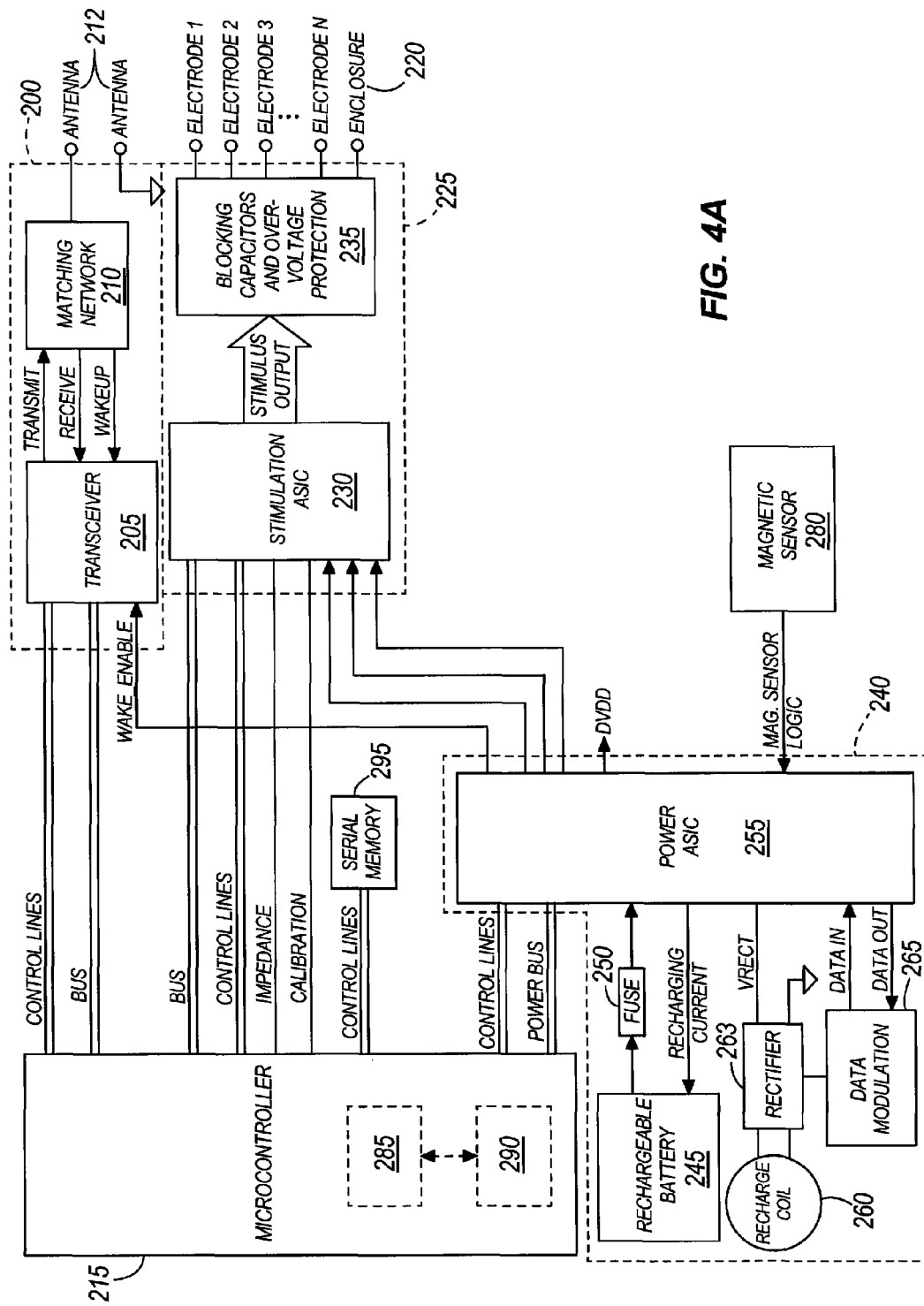
FIG. 4A is a block diagram of an implantable pulse generator for use in the spinal cord stimulation system of FIG. 1.
Figure 4B:
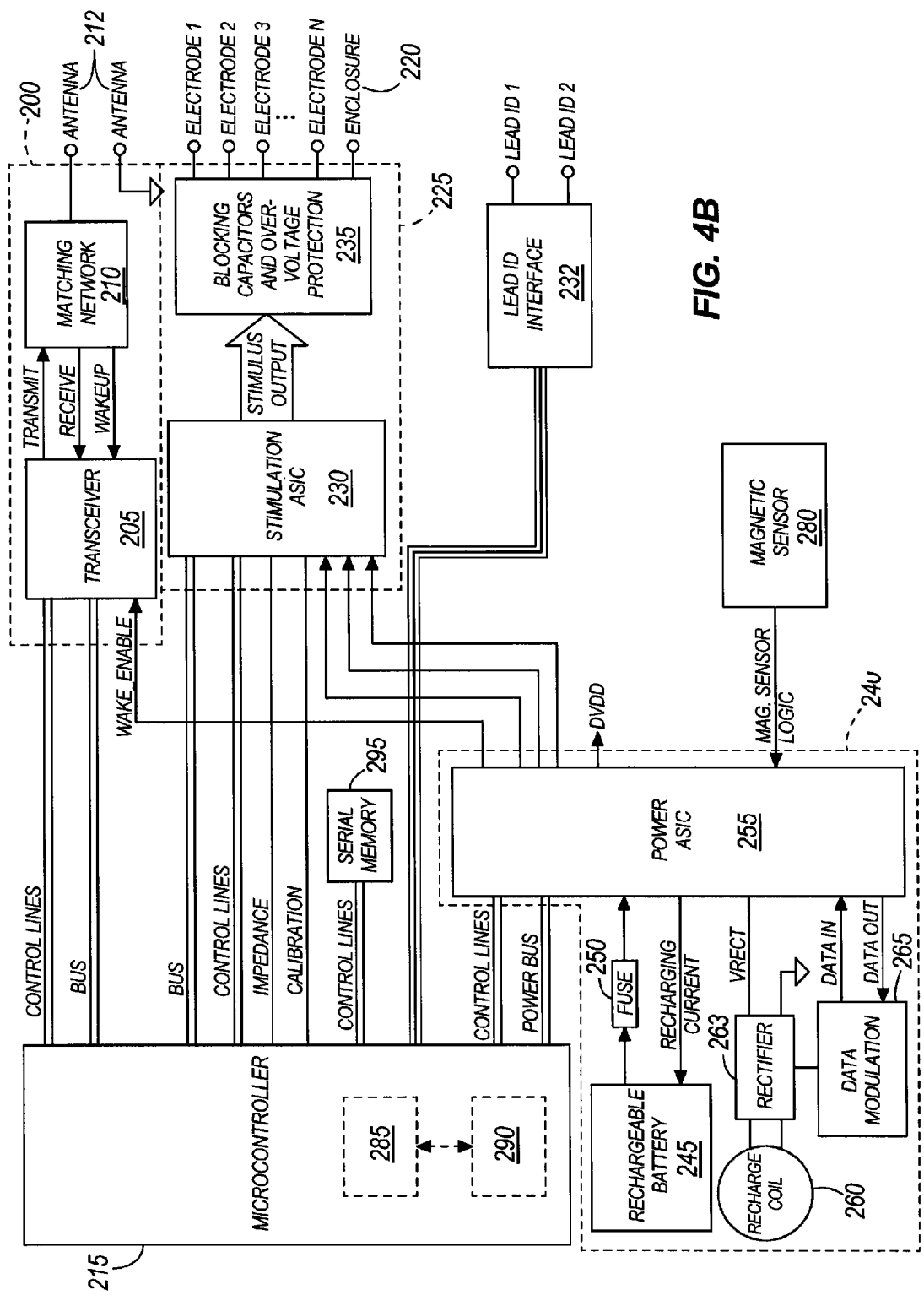
FIG. 4B is a block diagram of an alternative implantable pulse generator for use in the spinal cord stimulation system of FIG. 1.

FIGS. 4A and 4B show block diagrams of two possible constructions of the IPG 115. The IPG 115 includes a printed circuit board ("PCB") that is populated with a plurality of electrical and electronic components that provide power, operational control, and protection to the IPG 115. With reference to FIGS. 4A and 4B, the IPG 115 includes a communication portion 200 having a transceiver 205, a matching network 210, and antenna 212. The communication portion 200 receives power from a power ASIC (discussed below), and communicates information to/from the microcontroller 215 and a device (e.g., the CP 130) external to the IPG 115. For example, the IPG 115 can provide bi-direction radio communication capabilities to allow an external programming device to send commands to the IPG 115 and to allow the IPG 115 to send status data and error codes back to the external programming device.

The IPG 115, as previously discussed, provides stimuli to electrodes 150 of an implanted medical electrode lead 110. As shown in FIGS. 4A and 4B, N electrodes 150 (addressed by the IPG 115 through respective channels) are connected to the IPG 115. In addition, the enclosure or housing 220 of the IPG 115 can act as an electrode. The stimuli are provided by a stimulation portion 225 in response to commands from the microcontroller 215. The stimulation portion 225 includes a stimulation application specific integrated circuit (ASIC) 230 and circuitry including blocking capacitors and an over-voltage protection circuit. As is well known, an ASIC is an integrated circuit customized for a particular use, rather than for general purpose use. ASICs often include processors and/or memory blocks including ROM, RAM, EEPROM, Flash, etc. The stimulation ASIC 230 can include a processor, memory, and firmware for storing preset pulses and protocols that can be selected via the microcontroller 215. The providing of the pulses to the electrodes 150 is controlled through the use of a waveform generator and amplitude multiplier of the stimulation ASIC 230. The stimulation portion 225 of the IPG 115 receives power from the power ASIC (discussed below). The stimulation ASIC 230 also provides signals to the microcontroller 215. More specifically, the stimulation ASIC 230 can provide impedance information for the channels associated with the electrodes 150, and also communicate calibration information with the microcontroller 215 during calibration of the IPG 115. Additionally, the stimulation ASIC 230 of the IPG 115 can provide identification information from any connected leads 110 that include identification modules 420 (discussed below) coupled through the electrode channels. In the construction shown in FIG. 4B, the IPG 115 includes a separate lead ID interface 232 which includes connections to identification modules 420 that are independent of the electrode channel connections. In this latter construction, the lead ID interface 232 is independent of the stimulation ASIC 230 and communicates identification information directly to the microcontroller 215.

The IPG 115 also includes a power supply portion 240. The power supply portion includes a rechargeable battery 245, fuse 250, power ASIC 255, recharge coil 260, rectifier 263 and data modulation circuit 265. The rechargeable battery 245 provides a power source for the power supply portion 240. The recharge coil 260 receives energy from the PPC 135 via an inductive link. The inductive link uses a primary coil connected to the PPC 135 to transfer energy inductively to the recharge coil 260, which behaves as a secondary coil in the inductive link. The energy received by the recharge coil 260 is converted and conditioned to a power signal by the rectifier 263. The power signal is provided to the rechargeable battery 245 via the power ASIC 255. The power ASIC 255 manages the power for the IPG 115. The power ASIC 255 provides one or more voltages to the other electrical and electronic circuits of the IPG 155. The data modulation circuit 265 facilitates the charging process by allowing bidirectional communications between the IPG 115 and PPC 135 via the inductive link.

The IPG 115 also includes a magnetic sensor 280. The magnetic sensor 280 provides a "hard" switch upon sensing a magnet for a defined period. The signal from the magnetic sensor 280 can provide an override for the IPG 115 if a fault is occurring with the IPG 115 and the IPG 115 is not responding to other controllers.

The IPG 115 is shown in FIG. 4 as having a microcontroller 215. Generally speaking, the microcontroller 215 is a controller for controlling the IPG 115. The microcontroller 215 includes a suitable programmable portion 285 (e.g., a microprocessor or a digital signal processor), a memory 290, and a bus or other communication lines.

The IPG 115 includes memory, which can be internal to the control device (such as memory 290), external to the control device (such as serial memory 295), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 285 executes software that is capable of being stored in the RAM, the ROM, or another non-transitory computer readable medium such as another memory or a disc.

Software included in the implementation of the IPG 115 is stored in the memory 290. The software includes, for example, firmware, one or more applications, program data, one or more program modules, and other executable instructions. The programmable portion 285 is configured to retrieve from memory and execute, among other things, instructions related to the control processes and methods described below for the IPG 115. For example, to enable a read mode of the lead identification module, the programmable portion 285 executes instructions for controlling the IPG 115 to provide a defined frequency or modulation on the channels that are in contact with the identification module 420. The defined frequency or modulation can be used to trigger a reading event of the module 420. Once the memory code string is received, the IPG 115 can process and make it available to other components, such as the CP 130.

The PCB also includes a plurality of additional passive and active components such as resistors, capacitors, inductors, integrated circuits, and amplifiers. These components are arranged and connected to provide a plurality of electrical functions to the PCB including, among other things, filtering, signal conditioning, or voltage regulation, as is commonly known.

Figure 5:
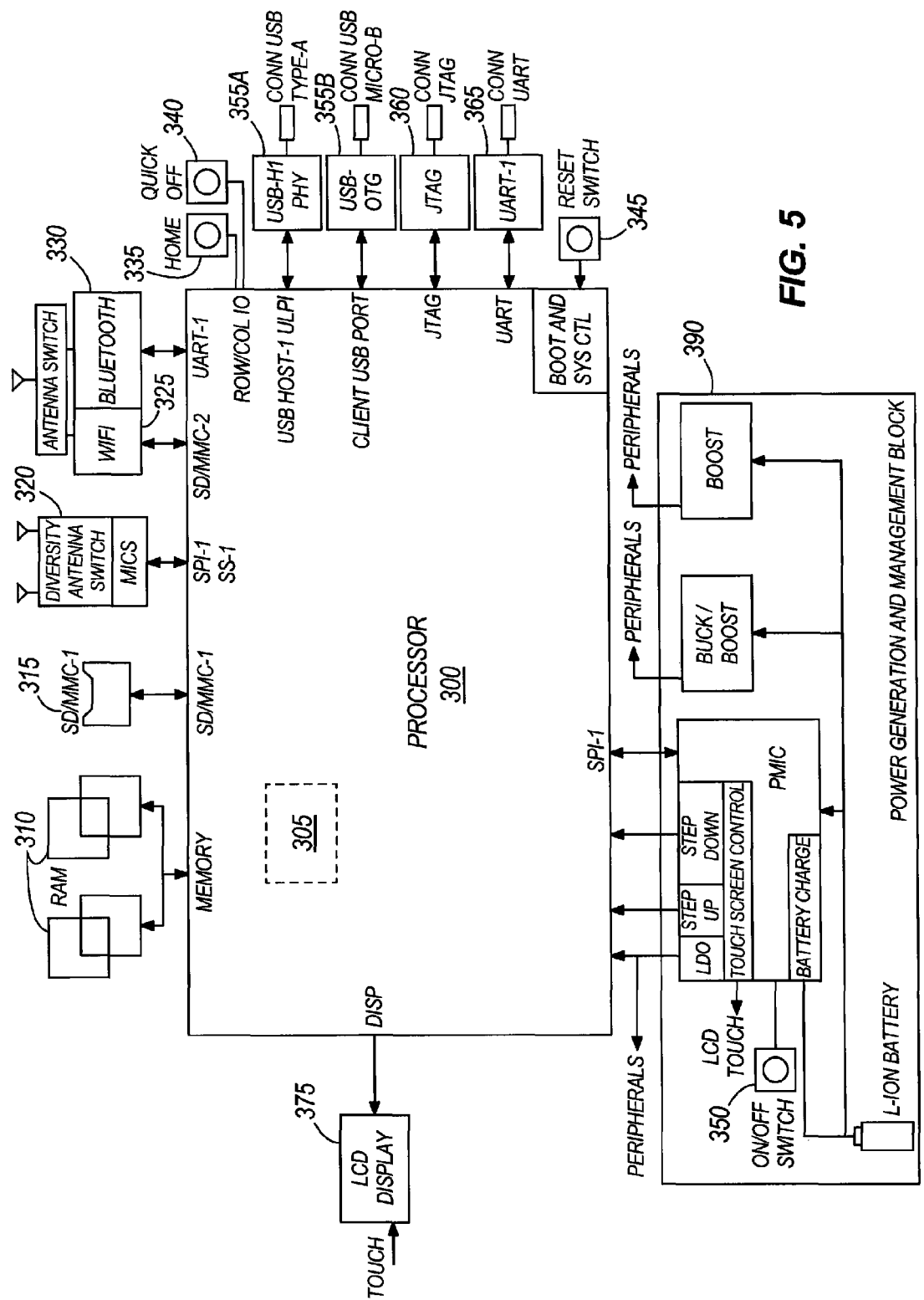
FIG. 5 is a block diagram of a clinician programmer for use in the spinal cord stimulation system of FIG. 1.

FIG. 5 shows a block diagram of one construction of the CP 130. The CP 130 includes a printed circuit board ("PCB") that is populated with a plurality of electrical and electronic components that provide power, operational control, and protection to the CP 130. With reference to FIG. 5, the CP includes a processor 300. The processor 300 is a controller for controlling the CP 130 and, indirectly, the IPG 115 as discussed further below. Of course, other processing units, such as other microprocessors, microcontrollers, digital signal processors, etc., can be used in place of the processor 300.

The CP 130 includes memory, which can be internal to the processor 300 (e.g., memory 305), external to the processor 300 (e.g., memory 310), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 300 executes software that is capable of being stored in the RAM, the ROM, or another non-transitory computer readable medium such as another memory or a disc. The CP 130 also includes input/output ("I/O") systems that include routines for transferring information between components within the processor 300 and other components of the CP 130 or external to the CP 130.

Software included in the implementation of the CP 130 is stored in the memory 305 of the processor 300, RAM 310, ROM 315, or external to the CP 130. The software includes, for example, firmware, one or more applications, program data, one or more program modules, and other executable instructions. The processor 300 is configured to retrieve from memory and execute, among other things, instructions related to the control processes and methods described below for the CP 130. For example, the processor 300 is configured to execute instructions retrieved from the memory 140 for establishing a protocol to control the IPG 115.

One memory shown in FIG. 5 is memory 310, which can be a double data rate (DDR2) synchronous dynamic random access memory (SDRAM) for storing data relating to and captured during the operation of the CP 130. In addition, a secure digital (SD) multimedia card (MMC) can be coupled to the CP for transferring data from the CP to the memory card via slot 315. Of course, other types of data storage devices can be used in place of the data storage devices shown in FIG. 5.

The CP 130 includes multiple bi-directional radio communication capabilities. Specific wireless portions included with the CP 130 are a Medical Implant Communication Service (MICS) bi-direction radio communication portion 320, a WiFi bi-direction radio communication portion 325, and a Bluetooth bi-direction radio communication portion 330. The MICS portion 320 includes a MICS communication interface, an antenna switch, and a related antenna, all of which allows wireless communication using the MICS specification. The WiFi portion 325 and Bluetooth portion 330 include a WiFi communication interface, a Bluetooth communication interface, an antenna switch, and a related antenna all of which allows wireless communication following the WiFi Alliance standard and Bluetooth Special Interest Group standard. Of course, other wireless local area network (WLAN) standards and wireless personal area networks (WPAN) standards can be used with the CP 130.

The CP 130 includes three hard buttons: a "home" button 335 for returning the CP to a home screen for the device, a "quick off" button 340 for quickly deactivating stimulation being delivered by the IPG 115, and a "reset" button 345 for rebooting the CP 130. The CP 130 also includes an "ON/OFF" switch 350, which is part of the power generation and management block 390.

The CP 130 includes multiple communication portions for wired communication. Exemplary circuitry and ports for receiving a wired connector include a portion and related port for supporting universal serial bus (USB) connectivity 355, including a Type-A port and a Micro-B port; a portion and related port for supporting Joint Test Action Group (JTAG) connectivity 360, and a portion and related port for supporting universal asynchronous receiver/transmitter (UART) connectivity 365. Of course, other wired communication standards and connectivity can be used with or in place of the types shown in FIG. 5.

The CP 130 includes a touch screen I/O device 375 for providing a user interface with the clinician. The touch screen display 375 can be a liquid crystal display (LCD) having a resistive, capacitive, or similar touch-screen technology. It is envisioned that multitouch capabilities can be used with the touch screen display 375 depending on the type of technology used.

Referring again to FIGS. 2A, 2B, and 3, the figures show constructions of implantable leads 110A (in-line lead), 110B (paddle lead), and 110C (lead extension), all of which have an identification module supported therein. For simplicity, the subsequent discussion will refer in general to the various types of leads using the generic identifier 110, however, the principles discussed herein are, for the most part, applicable to any of the three types of leads 110A, 110B or extensions 110C identified above as well as other types of implantable leads.

Figure 3:
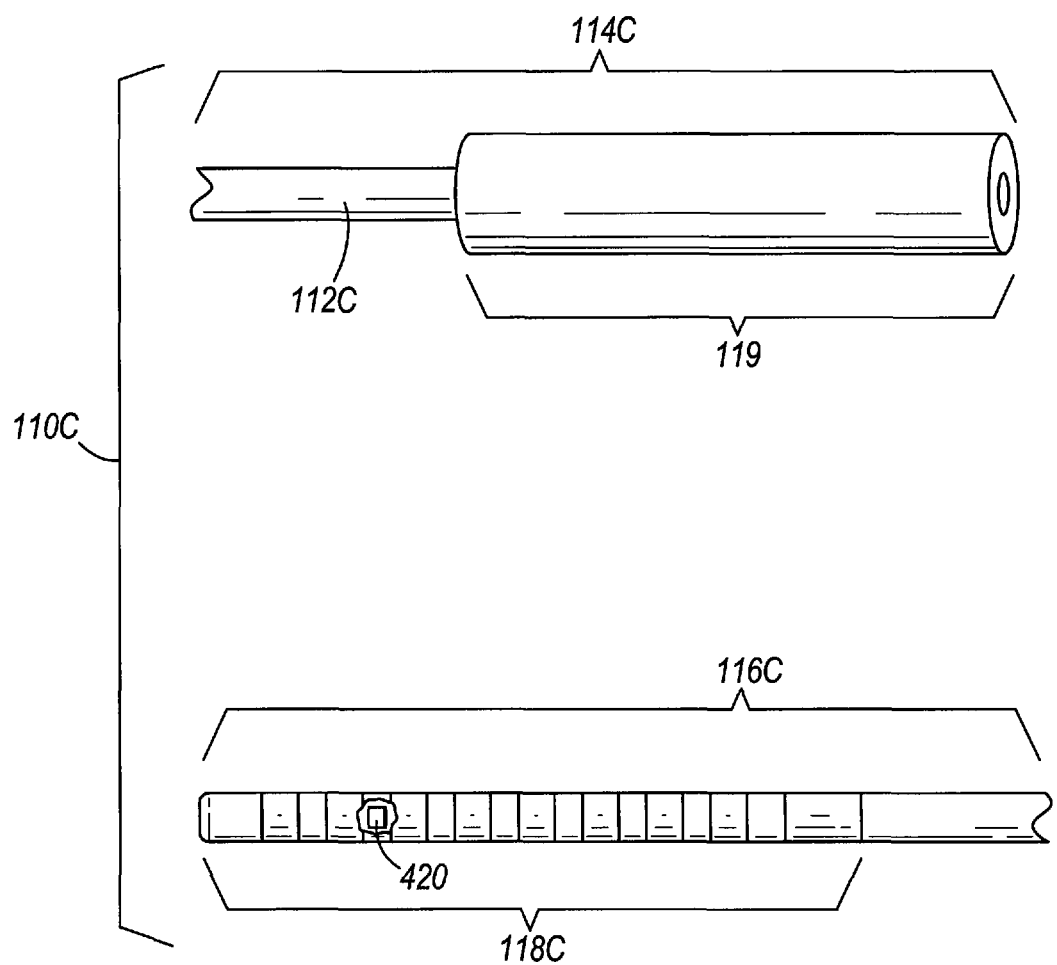
FIG. 3 is a perspective view of a lead extension for use in the spinal cord stimulation system of FIG. 1.
Figure 8:
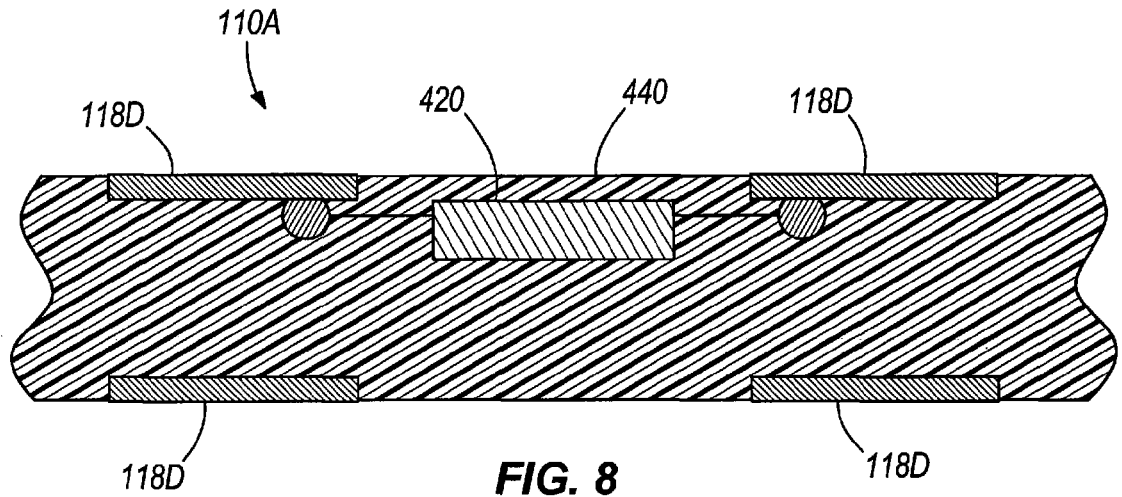
FIG. 8 is a longitudinal section view of a proximal connector.

In various constructions, a lead 110A, 110B includes a flexible lead body 112A, 112B having a distal end 114A, 114B and a connector end 116A, 116B. At the connector end 116A, 116B is a connector 118A, 118B which connects to the IPG 115 or to lead extension 110C. In various embodiments, the connector 118A, 118B includes one or more contacts 118D, which make electrical contact with complementary mating contacts in an appropriate receptacle such as in the IPG 115 or lead extension 110C. In certain embodiments, the contacts 118D are bands that encircle the connector end 116A, 116B (FIGS. 2A and 2B). At the distal end 114A, 114B are one or more electrodes 150A, 150B, each of which can be individually stimulated. The lead extension 110C includes a flexible extension body 112C with a distal end 114C, which couples to the lead 110A, 110B, and a proximal end 116C, which couples to the IPG 115. The proximal end 116C includes a connector 118C to connect to the IPG 115 and the distal end 114C includes a connector 119 to connect to a lead 110A, 110B. In various embodiments, the connector 118C includes one or more contacts 118D as described above and as shown in FIG. 3. The electrodes 150B of the paddle-style lead 110B are arranged on the face or platform 160 portion of the lead 110B. Each of the plurality of electrodes 150A, 150B is connected to a respective conductor 430 (e.g. wire), where the conductors 430 run through a flexible cable 155A, 155B. The flexible cable 155A, 155B couples to an implantable pulse generator (IPG) 115 via a suitable connector, although in some constructions lead extensions 110C are used to connect leads 110A, 110B indirectly to the IPG 115. In various constructions, an identification module 420 includes a memory circuit for storing an identification code. The identification module 420 may be located in various places on the lead 110A, 110B, although in one construction the identification module 420 is located in or near the connector 118A, 118B in the vicinity of the contacts 118D (FIGS. 2A, 2B) and in some constructions the identification module 420 may be directly coupled to the contacts (FIG. 8). In the lead extension 110C, the identification module 420 may also be located in various places, although in one construction the identification module 420 is located in the connector 118C portion of the lead extension 110C (FIG. 3).

In an alternative to the IPG 115, in some constructions the leads 110A, 110B can receive electrical stimuli from an external pulse generator (EPG) 115A (also referred to a trial stimulator) through one or more percutaneous lead extensions (FIG. 1). An EPG 115A may be used during a trial period or when the amount of stimulation provided to the patient 105 would drain the power storage device in short durations.

Figure 6:
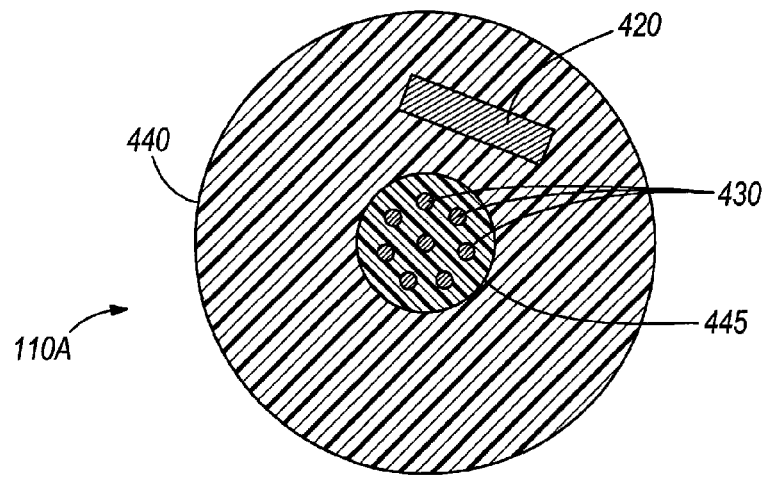
FIG. 6 is a cross section view of an in-line lead.
Figure 7:
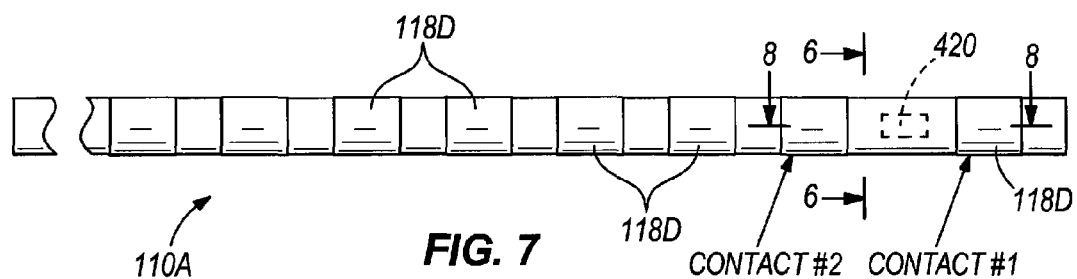
FIG. 7 is a side view of a proximal connector.

In various constructions, the identification module 420 may be embedded within the body of a lead 110A, 110B, or 110C. In one construction of an in-line lead 110A, the cross-section of which is shown in FIG. 6, the lead 110A includes an outer wall 440 and a cavity 445 in the center through which the conductors 430 run. In one particular construction, the wall 440 is sufficiently thick so as to accommodate the identification module 420 therein (see, e.g., FIG. 6). In general, in-line leads 110A include a plurality of electrodes that typically include circumferential bands of conductive material wrapped around or embedded in an insulating body, where the electrodes are spaced apart along the length of the lead. In some constructions, the identification module 420 is located in the space between contacts 118D (FIGS. 2A, 2B), generally embedded within insulating material of the lead 110A, 110B or extension 110C (FIG. 6).

Figure 9:
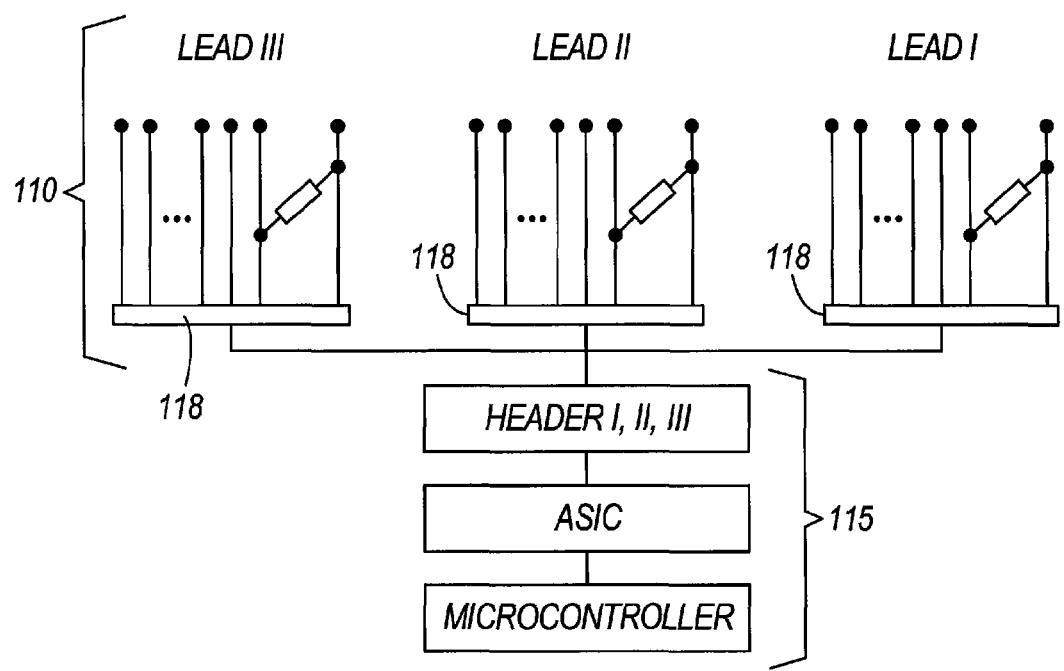
FIG. 9 is a schematic diagram of three leads, each having an identification module incorporated therein.

In the constructions in which an identified in-line lead 110A has an identified extension lead 110C attached to it, the IPG 115 (or EPG) reads separate identification modules 420 associated with both the in-line lead 110A and the extension lead 110C. To facilitate separate reading of each identification module 420, in some constructions, the identification module 420 in the extension lead 110C is located on a separate set of conductors 430 than the identification module 420 in the primary lead 110A (FIG. 9).

Figure 10:
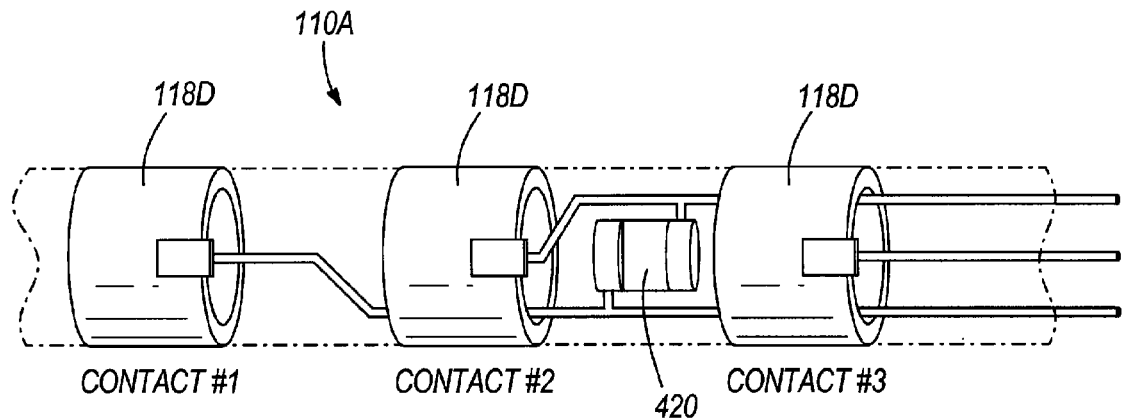
FIG. 10 is a diagram of an identification module embedded within an in-line lead.

The identification module 420 in certain constructions may be encapsulated with a protective material prior to, or coincident with, being embedded in the insulating material of the lead 110A. In various constructions, the identification module 420 is encapsulated in a material such as glass, ceramic, polymer, stainless steel, or other material. Glasses suitable for hermetically sealing and encapsulating the identification module 420 are manufactured, for example, by Schott glass of Germany. Bio-compatible polymers may also be used to encapsulate and hermetically seal the identification module 420. For example, FIG. 10 schematically depicts a glass-encapsulated identification module 420 disposed between two contacts 118D in the connector end of an in-line lead 110A. The encapsulated identification module 420 has two leads to which conductors can be welded or attached through some other means during lead assembly, or the leads of the identification module 420 can be directly connected to contacts 118D on the connector 118A, 118B, 118C (FIG. 8).

Known materials and methods already in use for construction of feed-through terminals for implantable medical devices can be used to encapsulate the module 420. The material may be selected to have one or more of the following properties: (1) biocompatibility with the tissue that the lead will be implanted into; (2) low fluid permeability, including the ability to prevent the ingress of bodily fluids into or near the module 420 and the ability to provide a suitable mechanical and fluid seal with respect to the electrical feed-through terminals through which electrical connections are established between the identification module 420 and electrical conductors in the lead 110; (3) MRI compatibility; heat stability during manufacturing (up to about 300° F.) and use; and (4) protection against leakage current and short circuiting. Thus, the identification module 420 can be hermetically sealed and provide suitable electrical connections thereto.

In general the identification module 420 (with encapsulation) is typically small enough to fit within whatever portion of the lead 110 it is placed into. In one construction the identification module 420 includes an EPROM. Other memory modules and various module sizes are envisioned to be possible for the identification module 420.

Figure 11:
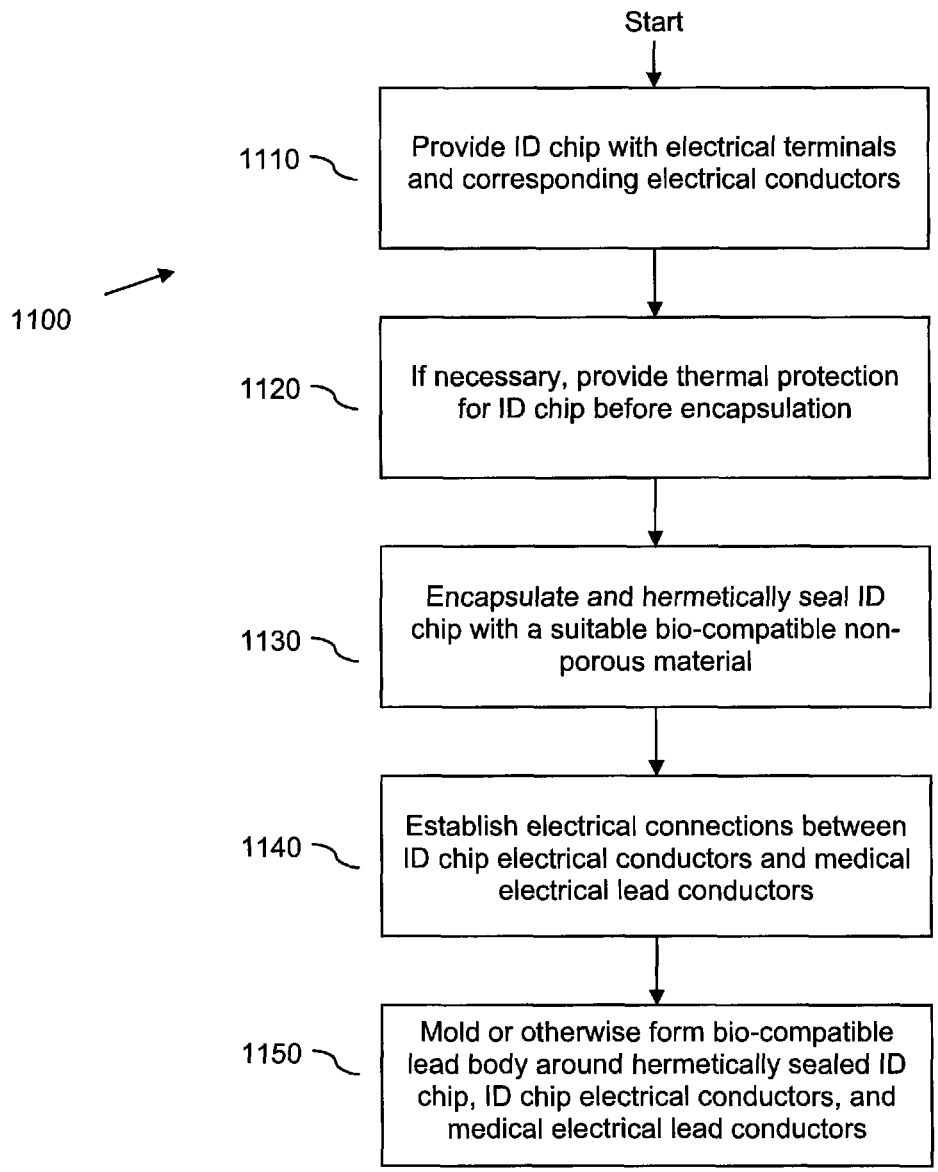
FIG. 11 is a flow diagram of a method of making an identification module.
Figure 15:
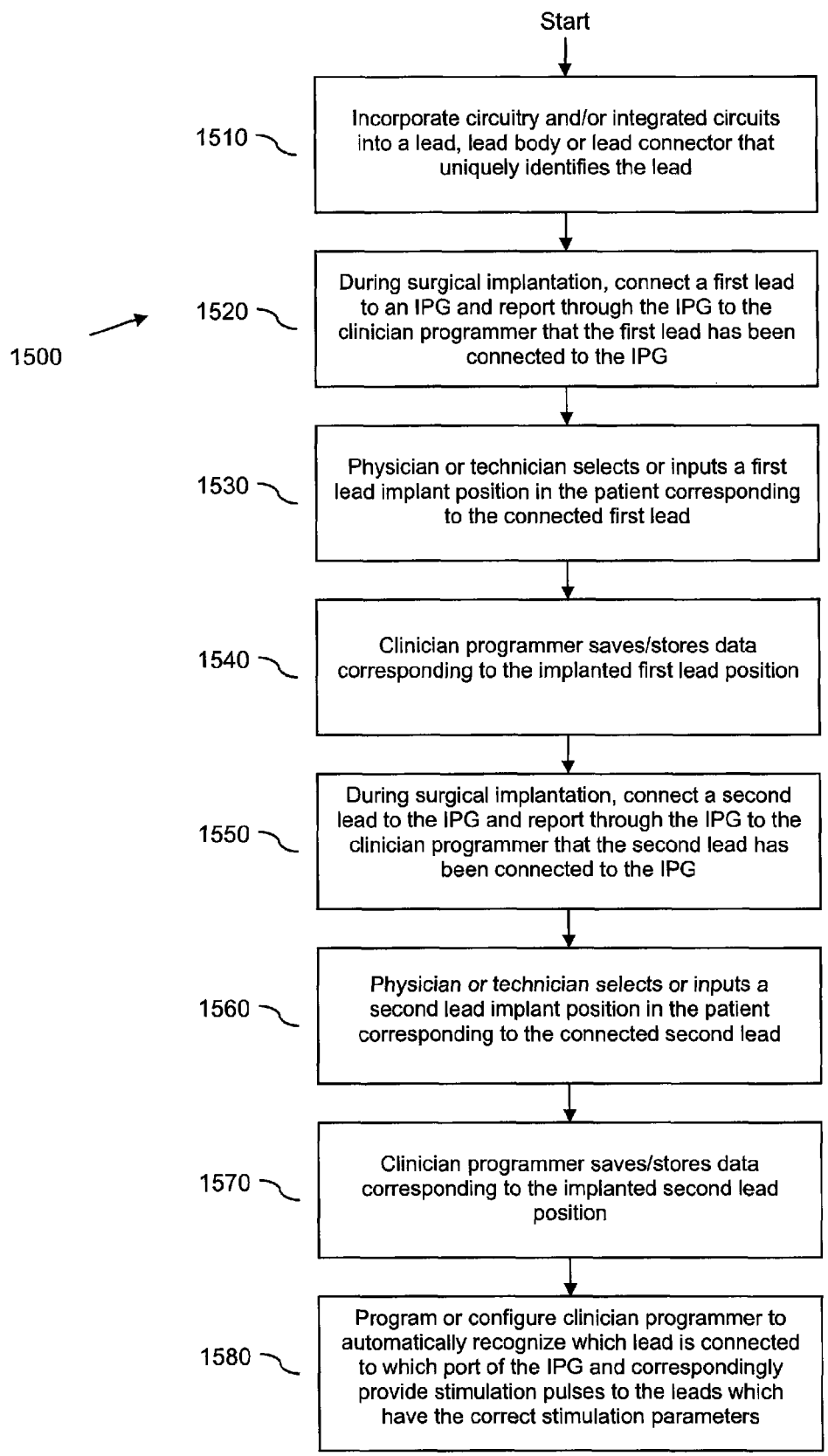
FIG. 15 is a flow diagram of a method of implanting an implantable pulse generator with one or more electrically identifiable lead.

Before proceeding further, it should be understood that the steps discussed in connection with FIGS. 11 and 15 will be discussed in an iterative manner for descriptive purposes. Various steps described herein with respect to the processes of FIGS. 11 and 15 are capable of being executed in an order that differs from the illustrated serial and iterative manner of discussion. It is also envisioned that not all steps are required as described below, that other steps may intervene the steps that are listed, and that one or more of the steps described with respect to each of the processes of FIGS. 11 and 15 can be carried out at the same time.

FIG. 11 shows a flowchart of one implementation of a method 1100 of making an identification module 420. A first step 1110 is providing an identification chip with electrical terminals and corresponding electrical conductors. A second step 1120, if necessary, is providing thermal protection for the identification chip before encapsulation. A third step 1130 is encapsulating and hermetically sealing the identification chip with a suitable bio-compatible, non-porous material. A fourth step 1140 is establishing electrical connections between the identification chip electrical conductors and medical electrode lead conductors. A fifth step 1150 is molding or otherwise forming a bio-compatible lead body around the hermetically sealed identification chip, the identification chip electrical conductors, and the medical electrode lead conductors.

Figure 12:
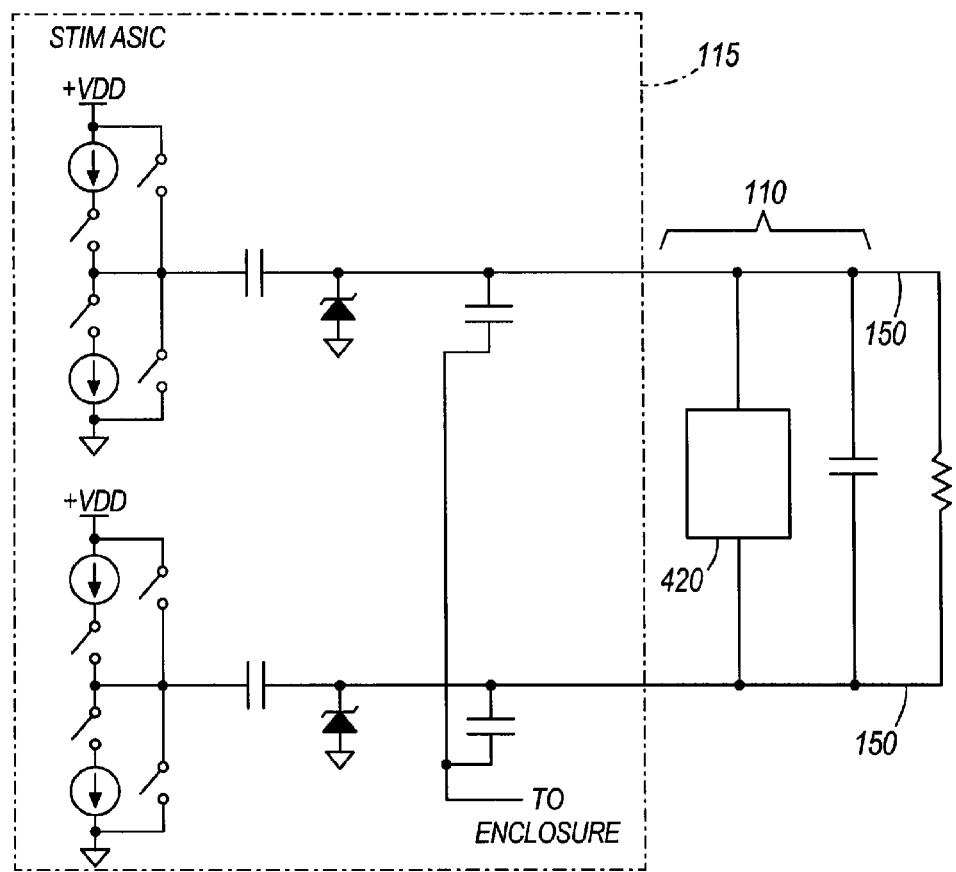
FIG. 12 is an electrical schematic of an implantable pulse generator coupled to a lead with an identification module electrically connected between two conductors of the lead.
Figure 13:
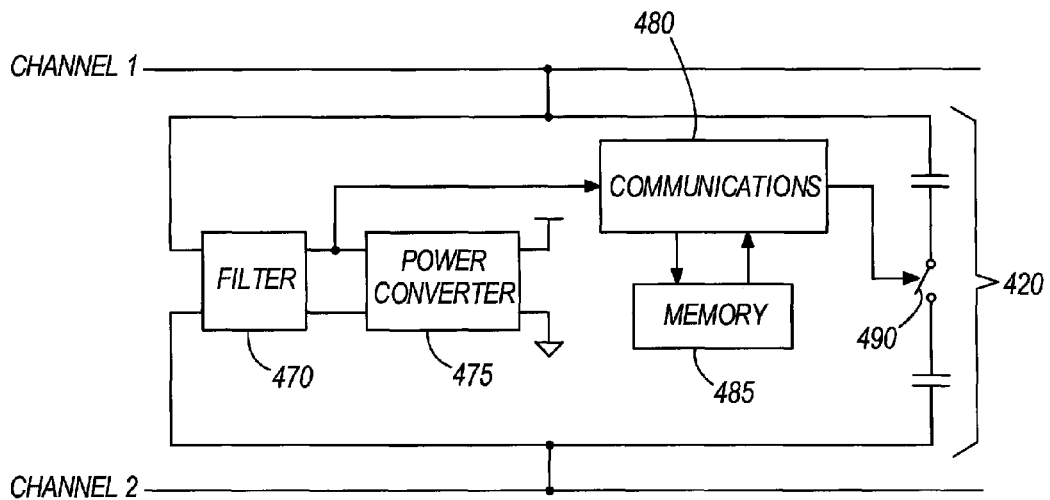
FIG. 13 is a circuit diagram of an identification module that uses two conductors without interrupting either of the conductors.
Figure 14:
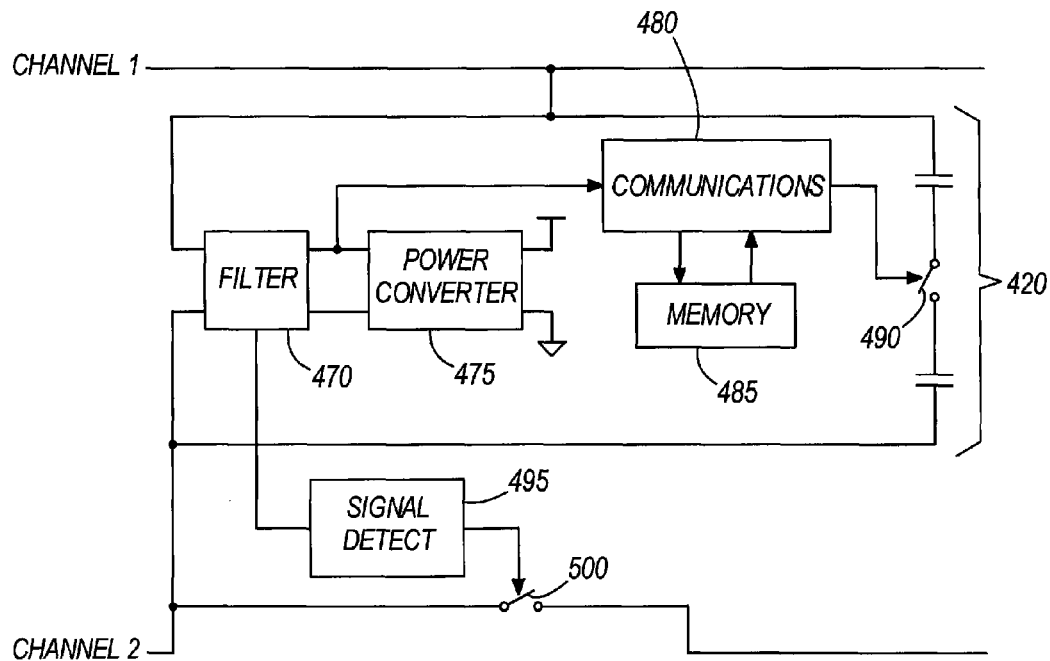
FIG. 14 is a circuit diagram of an identification module that uses two conductors but includes a switch that can interrupt one of the conductors.

FIG. 12 shows the electrical environment of the identification module 420 and FIGS. 13-14 show possible arrangements for a two-contact (FIG. 13) and a three-contact (FIG. 14) circuit for use in the identification module 420.

FIG. 12 shows a simplified circuit model of an IPG 115 having a lead 110 attached thereto, the lead 110 having an identification module 420 electrically connected between two electrodes 150 of the lead 110. The circuit model also includes the capacitance between the channels, which in this construction is typically tens of picofarads, as well as the resistance/impedance of the tissue ($R_{TISSUE}$), which in various constructions is between hundreds of ohms and several kilo-ohms.

One difficulty that arises from the electrical environment in which the identification module 420 operates is in powering the module 420, since the IPG 115 generates current, in some embodiments, instead of voltage. The voltage drop between the channels driving the module can be especially low if the tissue impedance is low. Thus, if the tissue impedance is 100Ω and the current delivered is 50 µA, then the voltage drop may be as low as 5 mV: 100 Ω×50 µA=5 mV. Accordingly, in some instances a "powering phase" may be required to build up an appropriate voltage in the module before reading the memory chip.

On the other hand, the electrical environment shown in FIG. 12 also indicates an advantage for the identification module 420, in some environments. Since there is a low impedance between the module 420 and the clamping circuit of the IPG 115, the module can rely on the voltage clamp of the IPG 115 without having to provide a voltage clamp circuit inside the identification module 420.

The construction of a two-contact circuit shown in FIG. 13 includes five circuit elements: a filter 470, a power converter 475, a communications circuit 480, a memory unit 485, and a load switch 490. The first two elements, filter 470 and power converter 475, take the incoming current and convert it to a voltage that is usable by the rest of the circuitry. The filter 470 has characteristics to prevent the identification module 420 from turning on during normal stimulation, while enabling the power converter 475 when the channels are driven in a specific manner. The communications circuit 480 transfers information from the memory unit 485 to the IPG 115 via load modulation using the load switch 490. In one construction, to read data from the memory unit 485 the IPG monitors the voltage drop between the two channels shown in FIG. 13. The communications circuit 480 opens and closes the load switch 490 in a predetermined pattern to transmit a code indicative of the lead identification (LID) for that lead 110. The opening and closing of the load switch 490 leads to comparable changes in the voltage that is required to maintain the constant current output of the channels. Accordingly, the time-based pattern of changes in voltage is recorded and decoded to determine the LID. In various constructions, the IPG 115 stores the information obtained from the lead(s) and/or transmits the information to another device such as CP 130, PPC 135, and/or UP 140 for subsequent review or retrieval by a health care provider.

A three-contact circuit (a construction of which is shown in FIG. 14) includes the same elements as the two-contact circuit and includes two additional elements, a signal detect circuit 495 and a channel switch 500. If an incoming read signal is detected by the signal detect circuit 495, the signal detect circuit opens the channel switch to permit the currentto-voltage conversion to proceed more quickly. When not activated, the channel switch 500 would default to a "closed" state.

In general, in the constructions of the identification module 420 disclosed herein there is no need for additional feedthrough terminals or lead contacts in order to allow lead identification. In other words, the identification module 420 uses the existing lead contacts for power to and communication with the identification module 420. When the identification module 420 is not communicating, the module 420 is "transparent" to the stimulation circuitry of the IPG 115. In various constructions, the identification module 420 has an impedance greater than 1 MΩ between its contacts when not being used.

As discussed above, constructions of the identification module 420 can be made using two contacts or three contacts, although in general the use of two contacts would be more desirable than three contacts from the standpoint of easier assembly with two contacts.

In various constructions, the identification module 420 is driven using a charge-balanced waveform, using either symmetric or asymmetric waveforms. In addition, the identification module 420 is generally driven with a sub-threshold current amplitude, e.g. using a current of 50 µA or less per phase. Likewise, the identification module 420 should be protected from currents arising in tissues from incoming external sources such as those associated with defibrillation pulses, electrocautery, or MRI. In general, the identification module 420 is capable of being driven by the normal output circuitry of the IPG 115, although additional circuitry may be required inside the IPG 115 for reading the identification data from the memory unit 185 of the identification module 420.

In various constructions the identification module 420 is capable of being read multiple times over the lifetime of the lead 110A, 110B. Although less preferred, one-time-read features, such as intentionally-blown fuses, can be included in the identification module 420.

As discussed above, the identification module 420, in some constructions, can be capable of communicating in the presence of a tissue impedance as low as 100Ω (target) between the leads to which the circuit is connected. In one construction, the identification module 420 is capable of storing up to 32 bytes of data, equal to 256 bits, although other levels of storage are also possible.

The above discussion describes locating the identification module 420 at the region of the lead 110A, 110B that includes the connector contacts 118D. Nevertheless, in various constructions the identification module 420 is located in other portions of the lead 110A, 110B such as the flexible lead body 155A, 155B or the distal end 114A, 114B, 114C.

The identifiable leads 110A, 110B, 110C disclosed herein can be used as part of means and methods for accurately, quickly, and reliably determining the types of leads that are connected to an implantable pulse generator (IPG) 115 and, in conjunction with positional information that is entered when each lead is implanted, their respective positions within the patient. Additionally, the above description provides an electronic identification system for implantable neurostimulation leads that is physically integrated into the lead body. Although the disclosure uses in-line leads 110A as examples, the disclosed methods and apparatus are equally applicable to other types of medical electrode leads, such as paddle-style leads 110B and extension leads 110C.

The invention herein relates to an electrical stimulation system for providing stimulation to target tissue of a patient. The system described in detail herein is a spinal cord stimulation (SCS) system for providing electrical pulses to the neurons of the spinal cord of a patient. However, many aspects of the invention are not limited to spinal cord stimulation. The electrical stimulation system may provide stimulation to other body portions, including a muscle or muscle group (including heart muscle, e.g. as part of a pacemaker), nerves, the brain, and other portions of the body.

In various constructions, the identification module 420 does not use non-contact, radio-based communication to interact with the IPG 115. Instead, the identification module 420 communicates with the IPG 115 directly via electrical connections, for example by connecting to the contacts 118D on the connector or the conductors 430 that connect the electrodes 150A, 150B with the IPG 115. In some constructions, the identification module 420 is connected to the conductors 430 themselves and in other constructions to the contacts 118D or electrodes 150, which in turn may be connected to the conductors 430.

In still other constructions, the identification module 420 is connected to a plurality (usually two) of contacts 118D that are not connected to conductors 430 or electrodes 150. In this latter case the operation of the identification module 420 would be less complicated since there would not be the difficulties associated with the low impedance between conductors 430 or electrodes 150 that is otherwise present. However, in this construction there may be two additional contacts 118D on the connector at the proximal end of the lead, which would be less desirable.

In use, leads and/or extensions send required data including, without limitation, a model number and a serial number to the IPG 115 and then to a device such as a clinician programmer 130 without having human interaction, which will reduce the time it takes for recording this information as well as the chance for error in recording such data.

Prior to or during the process of surgical implantation, each lead is implanted and connected to the IPG 115 (or EPG), which device then reads self-identifying data from the identification module 420 and can transmit this information to an external device such as CP 130. This process is then repeated for each lead that is implanted.

In various embodiments, the invention includes a method 1500 of implanting an identifiable lead, which method 1500 includes the following steps (see also FIG. 15):

A first step 1510 of providing an electrode lead having circuitry and/or integrated circuits incorporated therein, wherein the circuitry and/or circuits uniquely identify the lead 110.

A second step 1520 in which, during surgical implantation, a first lead 110 is connected to the IPG 115 and it is reported through the IPG 115 to the clinician programmer 130 (or other external device) that the first lead has been connected to the IPG 115 as well as the identification information (the lead identification, LID) obtained from the implanted lead 110.

A third step 1530 in which the physician or technician manually selects or inputs a first lead 110 implant position in the patient corresponding to the connected first lead 110 and stores this body location (BL). This BL will be stored (e.g. on the CP 130) along with the LID code that is electronically read from the lead 110.

A fourth step 1540 in which the clinician programmer 130 saves/stores data corresponding to the position of the implanted first lead 110.

A fifth step 1550 in which, during surgical implantation, a second lead 110' is connected to the IPG 115 and its presence is reported through the IPG 115 to the clinician programmer 130.

A sixth step 1560 in which the physician or technician manually selects or inputs a second lead 110' implant position in the patient corresponding to the connected second lead 110'.

A seventh step 1570 in which the clinician programmer 130 saves/stores data corresponding to the position of the implanted second lead 110'.

An eighth step 1580 in which the clinician programmer 130 is programmed or configured to automatically recognize which lead is connected to which port of the IPG 115 and correspondingly provide stimulation pulses having the correct stimulation parameters to the leads.

The leads 110 do not have to be attached to the IPG 115 in any particular order, since each lead 110 is capable of being uniquely identified using electronic means. As noted above, the BL of a particular lead is stored along with the LID for that lead, in addition to the Connector Number (CN) on the IPG 115 to which the lead 110 is attached. This information can be stored in one or more of the IPG 115, CP 130, PPC 135, or UP 140.

In various constructions, upon reading of an LID code, the CP 130, PPC 135, or UP 140 prompts a user (e.g. physician or technician) to assign a BL code to that particular lead. However, at some point (e.g. during programming of the IPG 115), the LID codes are synchronized with other stored information (e.g. CN, BL) on the IPG 115 so that such information will be available independent of which external device (e.g. which CP 130, PPC 135, or UP 140) is used. Thus, information including LID, CN, and BL is transmitted between the various elements of the system 100, e.g. by wired or wireless communication as appropriate, either as an automatic feature during communication or in response to a specific request or during a synchronization step.

During implantation, the physician or technician repeats the data reading and recording steps for each implanted lead. LID codes for extension leads, if any, are read and assigned together with the attached stimulation lead(s).

As discussed above, during implantation information regarding the position of implanted leads 110 is entered by a physician or clinician, e.g. after being prompted by a device such as the CP 130, PPC 135, or UP 140. In addition to the location (e.g. regarding which vertebra the lead 110 is implanted next to) other information that can be entered includes orientation of the lead 110. The orientation might be expressed relative to a reference point (e.g. the spinal column) including an indication of whether the lead 110 has its distal end 114A, 114B pointing up or down, left or right, or at a particular angle. The information regarding the position and orientation can then be used later when programming the lead 110.

Thus, in various constructions the invention provides a useful and novel system and method of identifying a lead and/or extension of an electrical stimulation system. Various features and advantages of the invention are set forth in the following claims.

What is claimed is:

1. An electrically identifiable medical electrode lead, comprising:
    a flexible lead body having a distal end and a connector end;
    a plurality of electrodes disposed near the distal end of the flexible lead body;
    a connector disposed at the connector end of the flexible lead body, the connector comprising a plurality of contacts;
    a plurality of conductors supported by and passing through the flexible lead body, the plurality of conductors including electrical conductors that provide paths for electrical current from the connector to the plurality of electrodes; and
    an identification module supported by the flexible lead body and being in electrical communication with a contact of the plurality of contacts in the connector,
    wherein the identification module is coupled to a first electrical conductor and a second electrical conductor of the plurality of conductors, and
    wherein the identification module is configured to communicate lead identification information based at least in part on a voltage difference between the first conductor coupled to the identification module and the second conductor coupled to the identification module.

2. The electrically identifiable medical electrode lead of claim 1, wherein the identification module includes a filter and a power converter.

3. The electrically identifiable medical electrode lead of claim 2, wherein the identification module includes a communications module.

4. The electrically identifiable medical electrode lead of claim 1, wherein the identification module includes a memory circuit storing an identification code.

5. The electrically identifiable medical electrode lead of claim 1, wherein the flexible lead body includes an outer wall and a cavity, wherein the outer wall surrounds the cavity along the length of the flexible lead body, wherein the plurality of conductors are positioned within the cavity, and wherein the identification module is embedded in the outer wall.

6. The electrically identifiable medical electrode lead of claim 5, wherein the identification module is embedded in the outer wall near the connector end of the flexible lead body.

7. The electrically identifiable medical electrode lead of claim 1, wherein the identification module is hermetically sealed within the flexible lead body.

8. The electrically identifiable medical electrode lead of claim 1, wherein the flexible lead body comprises glass and the identification module is sealed in the glass.

9. The electrically identifiable medical electrode lead of claim 1, wherein the distal end of the flexible lead body comprises a paddle lead or an in-line lead.

10. The electrically identifiable medical electrode lead of claim 1, wherein the identification module further includes a memory and a controllable load switch, and wherein the identification module is configured to control the voltage difference between the first conductor and the second conductor by opening and closing the load switch based on lead identification information stored in the memory.

11. An electrical stimulation system, comprising:
    an implantable pulse generator having a connection for at least one lead; and
    an electrically identifiable medical electrode lead, comprising
    a flexible lead body having a distal end and a connector end;
    a plurality of electrodes disposed near the distal end of the flexible lead body;
    a connector disposed at the connector end of the flexible lead body, the connector comprising a plurality of contacts;
    a plurality of conductors supported by and passing through the flexible lead body, the plurality of conductors including electrical conductors that provide paths for electrical current from the connector to the plurality of electrodes; and a first identification module supported by the flexible lead body and being in electrical communication with a contact of the plurality of contacts in the connector, wherein the first identification module is coupled to a first electrical conductor and a second electrical conductor of the plurality of conductors, and wherein the first identification module is configured to communicate lead identification information based at least in part on a voltage difference between the first conductor coupled to the first identification module and the second conductor coupled to the first identification module.

12. The system of claim 11, further comprising an electrically identifiable medical lead extension coupled to the lead, the extension comprising a flexible extension body having a proximal end and a distal end;

a proximal connector disposed at the proximal end of the flexible extension body and coupled to the implantable pulse generator, the proximal connector comprising a plurality of contacts;

a distal connector disposed at the distal end of the flexible extension body and coupled to the connector end of the identifiable medical electrode lead;

a plurality of conductors supported by and passing through the flexible extension body, the plurality of conductors including electrical conductors that provide paths for electrical current from the proximal connector to the distal connector; and a second identification module supported by the flexible extension body and being in electrical communication with a contact of the plurality of contacts in the proximal connector.

13. The system of claim 12, wherein at least one of the first identification module and the second identification module stores an identification code.

14. The system of claim 11, wherein the implantable pulse generator comprises an implantable neurostimulator.

15. The system of claim 11, wherein the identification module includes a filter and a power converter.

16. The system of claim 15, wherein the identification module further includes a communications module.

17. The system of claim 11, wherein the flexible lead body includes an outer wall and a cavity, wherein the outer wall surrounds the cavity along the length of the flexible lead body, wherein the plurality of conductors are positioned within the cavity, and wherein the first identification module is embedded in the outer wall of the flexible lead body.

18. The system of claim 11, wherein the first identification module is hermetically sealed within the flexible lead body.

19. The system of claim 11, wherein the first identification module is sealed in glass within the flexible lead body.

20. The system of claim 11, wherein the distal end of the flexible lead body comprises a paddle lead or an in-line lead.

21. The electrical stimulation system of claim 11, wherein the first identification module further includes a memory and a controllable load switch, and wherein the first identification module is configured to adjust the voltage difference between the first conductor and the second conductor by opening and closing the load switch based on lead identification information stored in the memory.

* * * * *